(12) United States Patent
Sontheimer et al.

(10) Patent No.: US 6,197,820 B1
(45) Date of Patent: Mar. 6, 2001

(54) USE OF PHENYLGLYCINE DERIVATIVES TO DECREASE NEURONAL DEATH CAUSED BY BRAIN TUMORS AND BRAIN LESIONS

(75) Inventors: Harald J. Sontheimer; Zu-Cheng Ye, both of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/292,029

(22) Filed: Apr. 16, 1999

Related U.S. Application Data
(60) Provisional application No. 60/080,859, filed on Apr. 6, 1998.

(51) Int. Cl.[7] .................................................. A61K 31/195
(52) U.S. Cl. ............................................................ 514/567
(58) Field of Search ............................................. 514/567

(56) References Cited

U.S. PATENT DOCUMENTS

| | | | |
|---|---|---|---|
| 5,610,183 | * 3/1997 | Owens et al. | 514/539 |
| 5,783,575 | * 7/1998 | Jakobsen et al. | 514/232.8 |
| 5,863,947 | * 1/1999 | Baker et al. | 514/567 |

FOREIGN PATENT DOCUMENTS

WO 95/15941 * 6/1995 (WO).

* cited by examiner

*Primary Examiner*—William R. A. Jarvis
(74) *Attorney, Agent, or Firm*—Benjamin Aaron Adler

(57) ABSTRACT

The present invention describes impaired glutamate uptake in glioma cells, and further shows that instead of removing glutamate from the extracellular fluid, glioma cells release large amounts of glutamate. The high levels of extracellular glutamate result in elevated $[Ca^{2+}]_i$ followed by widespread neuronal death, which could be prevented by treating neurons with the NMDA receptor antagonists, MK-801 or D-AP5, or by depletion of glutamate from the medium. Significantly, several phenylglycine derivatives, including the metabotropic glutamate receptor agonist/antagonist (S)-4-carboxyphenylglycine (S-4CPG), potently and selectively inhibited glutamate release from glioma cells and thereby prevented neurotoxicity.

7 Claims, 14 Drawing Sheets

USE OF PHENYLGLYCINE DERIVATIVES TO DECREASE NEURONAL DEATH CAUSED BY BRAIN TUMORS AND BRAIN LESIONS

This application claims priority to provisional application No. 60/080,859, filed Apr. 6, 1998. +gi

FEDERAL FUNDING LEGEND

This invention was produced in part using funds under grants R01-NS-31234 and P50-HD-32901 from the National Institutes of Health. Consequently, the federal government has certain rights in this invention.

BACKGROUND OF THE INVENTION

1. Field of the Invention

The present invention relates generally to the field of neurobiology. More specifically, the present invention relates to compounds, specifically phenylglycine derivatives, that inhibit the release of toxic levels of glutamate from brain tumor cells.

2. Description of the Related Art

L-glutamate is an important nutritional amino acid involved in a number of biochemical pathways. Glutamate is also the main excitatory amino acid transmitter in the mammalian central nervous system. Extracellular glutamate concentrations are normally maintained at low micromolar levels to assure proper synaptic function and to prevent excitotoxic injury of neurons (1,2). This is accomplished through the activity of several $Na^+$-dependent glutamate transporters expressed by neurons and astrocytes. Of the 5 glutamate transporter subtypes cloned (3–7), two, namely GLAST and GLT-1, appear to be predominantly located on glial cells (8,9).

It is believed that astrocytes, which comprise a large portion of the total cell population in the mammalian nervous system, are particularly important in maintaining glutamate homeostasis (10–13), since their processes closely encapsulate synapses and they are invulnerable to glutamate challenge. Like neurons, astrocytes maintain a large transmembrane glutamate gradient, with intracellular glutamate concentrations of 2–10 mM (14–16), while the $[Glu]_o$ is approximately 1 $\mu$M (2,17). Since astrocytic glutamate transport is electrogenic and uses the transmembrane electrochemical gradient for $Na^+$, $K^+$ and $H^+$ (18,19), severe disruption of these gradients, or membrane depolarization under conditions of energy failure (ischemia, hypoglycemia), can lead to glutamate release from astrocytes by reversal of glutamate transport (20–22).

Unlike neurons, glial cells retain the ability to proliferate post-natally. Uncontrolled, cancerous proliferation of glial cells results in primary brain tumors, collectively termed gliomas. The vast majority of gliomas originate through the neoplastic transformation of astrocytes. Astrocyte-derived tumors often develop over the course of many months to years, beginning as slowly growing low-grade astrocytomas and progressing towards more aggressive astrocytomas that eventually can give rise to gliobastoma multiforme, the most aggressive glial-derived tumors.

The cellular and functional changes that accompany the malignant transformation of astrocytes is poorly understood. As in other cancers, a number of genetic alterations precede the malignant phenotype and are conspicuous features, including upregulation of growth factor receptors, and changes in extracellular matrix molecules (24) and focal adhesion sites (25). Neovasularization and focal necrosis are also consistent features of high grade gliomas (26). It is not clear if or how the growing tumor mass causes neuronal cell death along the growing tumor margins. However, epileptic seizures, as an indicator of compromised neural function, are commonly associated with brain tumors (27).

It is shown herein that glioma cells are impaired in their ability to remove glutamate from the extracellular space, and in addition, actively release glutamate at concentrations that can induce widespread neurotoxicity. This finding suggests that tumors may actively induce neuronal death at the growing tumor margins and that glutamate release by tumors may contribute to seizure activity arising from peritumoral brain regions.

The prior art is deficient in compositions and methods that inhibit the toxic release of glutamate from brain tumor cells. The present invention fulfills this long-standing need and desire in the art.

SUMMARY OF THE INVENTION

Glutamate excitotoxicity as been proposed to be the final common pathway in a number of nervous system diseases, including stroke, ALS, Huntington's disease, Alzheimer's disease and AIDS dementia (1,23). The present invention describes a role for glutamate toxicity associated with the progression of brain tumors, a disease not previously implicated with glutamate toxicity.

The present invention describes glutamate uptake in glioma cells. All glioma cells studied showed impaired glutamate uptake, with maximum transport rates of less than 5% of normal astrocytes. Moreover, instead of removing glutamate from the extracellular fluid, glioma cells release large amounts of glutamate. Exposure of cultured hippocampal neurons to glioma-conditioned medium, or co-culturing of hippocampal neurons and glioma cells, either with or without direct contact, elicited sustained $[Ca^{2+}]_i$ elevations that were followed by widespread neuronal death. Data presented herein demonstrates that glioma-induced neuronal death could be prevented by treating neurons with the NMDA receptor antagonists, MK-801/D-AP5, or by depletion of glutamate from the medium. Significantly, several phenylglycine derivatives, including the metabotropic glutamate receptor agonist/antagonist (S)-4-carboxyphenylglycine (S-4CPG), potently and selectively inhibited glutamate release from glioma cells and thereby prevented neurotoxicity.

One object of the present invention is to provide compositions that inhibit the release of toxic levels of glutamate by glial cells and methods of using those compositions.

In an embodiment of the present invention, there is provided a method of decreasing neuronal death in an individual, comprising the step of: administering to the individual a pharmacologically effective dose of a phenylglycine derivative, wherein the phenylglycine derivative results in a decrease in the amount of glutamate released from the cells, thereby decreasing neuronal death in the individual.

In an embodiment of the present invention, there is provided a method of inhibiting the amount of glutamate released from cells, comprising the step of: contacting the cells with a pharmacologically effective dose of a phenylglycine derivative. The phenylglycine derivative results in an inhibition in the amount of glutamate released from cells.

In yet another embodiment of the present invention, there is provided a method of treating epileptic seizures due to glutamate neurotoxicity in an individual, comprising the step of: administering to the individual a pharmacologically effective dose of a phenylglycine derivative. The phenylglycine derivative reduces extracellular glutamate levels, thereby treating the epileptic seizures.

In still yet another embodiment of the present invention, there is provided a pharmaceutical composition for decreasing extracellular glutamate levels, comprising: a phenylglycine derivative; and a pharmaceutically acceptable carrier.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1 shows glutamate uptake into astrocytes, human glioma cell lines and primary cultures from human biopsy tissues.

FIG. 2 shows that glioma cells release glutamate.

FIG. 3 shows that S-4CPG and other phenylglycine derivatives suppress glioma glutamate release in a dose-dependent manner.

FIG. 4 shows neuronal $[Ca^{2+}]_i$ responses to glioma-conditioned media or glioma cell suspensions.

FIG. 5 shows excitotoxicity from glioma-conditioned media and prevention by S-4CPG.

FIG. 7 shows excitotoxicity in glioma-neuronal co-cultures without direct contact.

DETAILED DESCRIPTION OF THE INVENTION

Figure 1B:
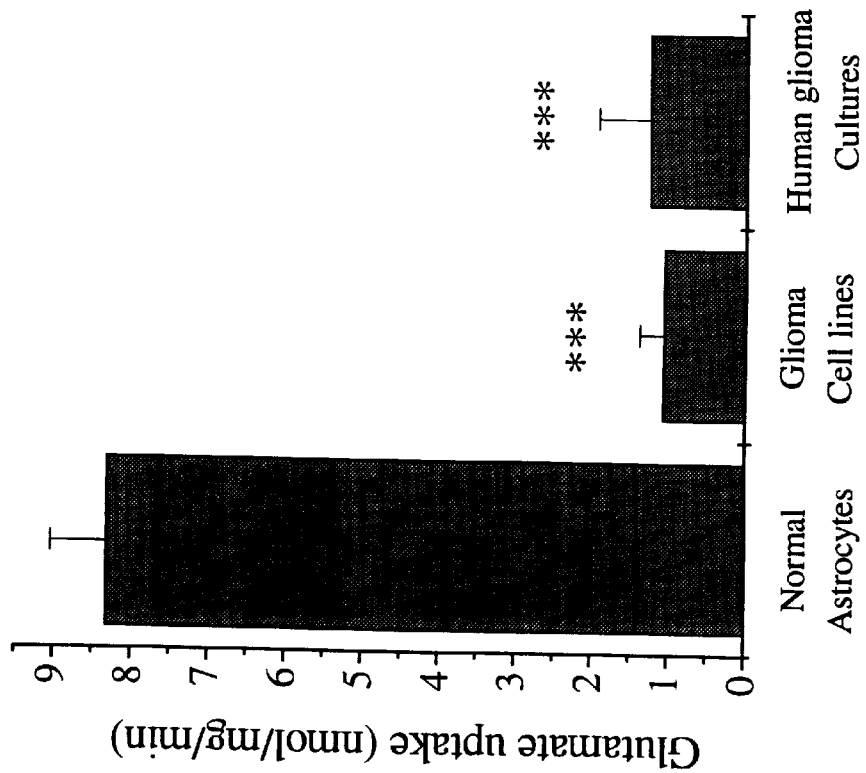
FIG. 1B: Mean glutamate uptake at 50 $\mu$M $[Glu]_o$ in astrocytes, 7 glioma cell lines (listed in panel A, average of the mean value of each cell line) and from 5 primary human glioma cultures (4 glioblastoma cases and one low grade astrocytoma). Glutamate uptake into glioma cells was significantly lower than astrocytes (n=6, *** $P<0.001$, t-test).

Elevated levels of extracellular glutamate ($[Glu]_o$) cause uncontrolled $Ca^{2+}$ increases in most neurons and are believed to mediate excitotoxic brain injury following stroke and other nervous system insults. In the normal brain, $[Glu]_o$ is tightly controlled by uptake into astrocytes. Since the vast majority of primary brain tumors (gliomas) are derived from astrocytes, glutamate uptake was investigated in glioma cells surgically isolated from glioma patients (glioblastoma multiforme) and in 7 established human glioma cell lines, including STTG-1, D-54MG, D-65MG, U-373MG, U-138MG, U-251MG and CH-235MG.

All glioma cells studied showed impaired glutamate uptake, with maximum transport rates of less than 5% of normal astrocytes. Moreover, rather than removing glutamate from the extracellular fluid, glioma cells release large amounts of glutamate, which result in elevations of $[Glu]_o$ in excess of 100 $\mu M$ within hours in a space which is $10^3$-fold larger than the cellular volume. Exposure of cultured hippocampal neurons to glioma-conditioned medium elicited sustained $[Ca^{2+}]_i$ elevations that were followed by widespread neuronal death. Similarly, co-culturing of hippocampal neurons and glioma cells, either with or without direct contact, resulted in neuronal death. Glioma-induced neuronal death could be completely prevented by treating neurons with the N-Methyl-D-aspartic acid (NMDA) receptor antagonists, MK-801 or D-AP5, or by depletion of glutamate from the medium. Significantly, several phenylglycine derivatives, including the metabotropic glutamate receptor agonist/antagonist (S)-4-carboxyphenylglycine (S-4CPG), potently and selectively inhibited glutamate release from glioma cells and prevented neurotoxicity.

These data suggest that growing glioma tumors may actively kill surrounding neuronal cells through release of glutamate, and that this glutamate release may also be responsible, in part, for tumor-associated seizures that frequently occur in conjunction with gliomas. These data also suggest that neurotoxic release of glutamate by gliomas may be prevented by phenylglycine derivatives, which may therefore be useful as an adjuvant treatment for brain tumors. The methods of the present invention may be extended to other brain tumors beside gliomas, as brain tumor cells also release glutamate and phenylglycine derivatives can inhibit the release. Moreover, these compounds may also be useful for other neuronal disease involve decreasing glutamate uptake and increasing glutamate release.

The present invention is directed towards a method of decreasing neuronal death in an individual, comprising the step of: administering to the individual a pharmacologically effective dose of a phenylglycine derivative, wherein the phenylglycine derivative results in a decrease in the amount of glutamate released from glioma cells, thereby decreasing neuronal death in the individual. Representative causes of neuronal death include primary brain tumors, metastatic brain tumor and mass brain lesion. Generally, the phenylglycine derivative is administered to the individual in an amount of from about 0.4 mg/kg to about 40 mg/kg.

The present invention is also directed towards a method of inhibiting the amount of glutamate released from cells, comprising the step of: contacting the cells with a pharmacologically effective dose of a phenylglycine derivative, wherein the phenylglycine derivative results in an inhibition in the amount of glutamate released from cells.

The present invention is further directed towards a method of treating epileptic seizures due to glutamate neurotoxicity in an individual, comprising the step of: administering to the individual a pharmacologically effective dose of a phenylglycine derivative, wherein the phenylglycine derivative reduces extracellular glutamate levels, thereby treating the epileptic seizures. Glutamate neurotoxicity may also be reduced by administration of the phenylglycine derivative prior to the epileptic seizure, thereby preventing the seizure. Representative causes of neuronal death include primary brain tumors, metastatic brain tumor and mass brain lesion. Typically, the phenylglycine derivative is administered to the individual in an amount of from about 0.2 mg/kg to about 40 mg/kg.

The present invention is still further directed towards a pharmaceutical composition for decreasing extracellular glutamate levels, comprising: a phenylglycine derivative; and a pharmaceutically acceptable carrier.

Preferable phenylglycine derivative useful to the present invention include (S)-4-Carboxyphenylglycine (S-4CPG), (RS)-3,5-Dihydroxyphenylglycine (DHPG), (S)-3-carboxy-4-hydroxyphenylglycine (S-3C4H-PG), (S)-4-carboxy-3-hydroxyphenylglycine (S-4C3H-PG), (R)-4-Carboxyphenylglycine (R-4CPG), (RS)-α-Ethyl-4-carboxyphenylglycine (E4CPG), (RS)-2-Chloro-5-hydroxyphenylglycine (CHPG), (RS)-2-Cyclopropyl-4-phosphonophenylglycine (CPPG), (S)-α-methyl-4-carboxyphenylglycine (MCPG), (RS)-α-methyl-4-tetrazolylphenylglycine (MTPG). The most preferable known phenylglycine derivative is (S)-4-Carboxyphenylglycine (S-4CPG).

A person having ordinary skill in this art would be able to manipulate the phenyglycine structure to generate compounds with even higher effects in inhibiting glutamate release from glioma and other brain tumor cells. For example, one may manipulate the attached group on the phenyl ring in phenylglycine derivatives. More specifically, the presence of a carboxy group in the phenyl ring can drastically increase the effect, however, it does not exclude the existence of any other compounds that do not have a phenylglycine backbone but structurally simulate S-4CPG.

As used herein, the term "neuronal death" refers to loss of viability and function of neurons.

As used herein, the term "phenylglycine derivative" refers to a group of chemical compounds related to phenylglycine, preferably with some modification on the phenyl ring, especially a carboxy group.

As used herein, the term "glioma cells" refers to primary brain tumor cells derived from glial cells by malignant neoplasmic transformation.

As used herein, the term "epileptic seizure" refers to repetitive spontaneous electrical discharges of a population of neuronal cells.

As used herein, the term "glutamate neurotoxicity" refers to excessive glutamate stimulation induced killing of neuronal cells.

It is specifically contemplated that pharmaceutical compositions may be prepared using the novel phenylglycine derivatives of the present invention. In such a case, the pharmaceutical composition comprises the novel phenylglycine derivatives of the present invention and a pharmaceutically acceptable carrier. A person having ordinary skill in this art would readily be able to determine, without undue experimentation, the appropriate dosages and routes of administration of this phenylglycine derivatives of the present invention. When used in vivo for therapy, the phenylglycine derivatives of the present invention are administered to the patient or an animal in therapeutically effective amounts, i.e., amounts that eliminate or reduce the tumor burden or neuronal injury. It will normally be administered parenterally, preferably intravenously, but other routes of administration will be used as appropriate. The dose and dosage regimen will depend upon the nature of the cancer (primary or metastatic) and its population, or alternatively, the nature of the neuronal injury, the characteristics of the particular phenylglycine derivatives (e.g., its therapeutic index), the patient, the patient's history and other factors. The amount of phenylglycine derivatives administered will typically be in the range of about 0.4 mg/kg of patient weight to about 40 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference. For parenteral administration, the phenylglycine derivatives will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The phenylglycine derivatives will typically be formulated in such vehicles at concentrations of about 2 mg/ml to 200 mg/ml.

The following examples are given for the purpose of illustrating various embodiments of the invention and are not meant to limit the present invention in any fashion:

EXAMPLE 1

Materials

The enzymes NAD(P)H:FMN oxidoreductase and glutamate dehydrogenase were purchased from Boehringer Mannheim (Indianapolis, Ind.). General cell culture supplies were obtained from Becton Dickinson (Franklin Lakes, N.J.) and Corning (Corning, N.Y.). Earle's Minimum Essential Media (MEM) and Dulbecco's Modified Eagle Medium (DMEM) were obtained from Life Technologies (Grand Island, N.Y.). Fetal bovine serum (FBS) was purchased from Hyclone (Logan, Utah). (S)-4-Carboxyphenylglycine (S-4CPG) was obtained from RBI (Natick, Mass.). D(−)-2-Amino-5-phosphonopentanoic acid (D-AP5), (RS)-3,5-Dihydroxyphenylglycine (DHPG), (S)-3-carboxy-4-hydroxyphenylglycine (S-3C4H-PG), (S)-4-carboxy-3-hydroxyphenylglycine (S-4C3H-PG), (R)-4-Carboxyphenylglycine (R-4CPG), MK 801, (RS)-α-Ethyl-4-carboxyphenylglycine (E4CPG), (RS)-2-Chloro-5-hydroxyphenylglycine (CHPG), (RS)-2-Cyclopropyl-4-phosphonophenylglycine (CPPG), (S)-α-methyl-4-carboxyphenylglycine (MCPG), (RS)-α-methyl-4-tetrazolylphenylglycine (MTPG) and 6-Cyano-7-nitroquinoxaline-2,3-dione (CNQX) were purchased from Tocris Cookson (Bristol, UK). All other enzymes and chemicals were purchased from Sigma (St. Louis, Mo.) unless stated otherwise.

EXAMPLE 2

Cell Lines and Primary Cultures of Human Astrocytomas

Glioma cell lines used in these studies included STTG1 [from American Type Culture Collection (ATCC), Manassas, Va.] and U-138MG, U-251MG, U-373MG, CH-235MG, D-54MG, D-65MG (all from Dr. D. D. Bigner, Duke University, Durham, N.C.). These cell lines were cultured in DMEM supplemented with 10% heat-inactivated FBS. Glioma cells were used 2–5 days after plating, at which time they had reached over 80% confluence. The majority of the excitotoxicity data reported herein was collected from STTG1 cells, and was subsequently confirmed using other glioma cell lines.

Primary cultures of human astrocytoma were established from freshly resected brain tumor biopsy tissues. Briefly, tumor tissues were freed of necrotic-hemorrhagic portions and minced to small pieces aseptically. This was followed by a 20 min digestion with 20 U/ml papain (Worthington, Freehold, N.J.) in an oxygen saturated solution consisting of 137 mM NaCl, 5.3 mM KCl, 1 mM $MgCl_2$, 25 mM Glucose, 10 mM HEPES, 3 mM $CaCl_2$, 0.5 mM EDTA, and 0.2 mg/ml L-cysteine. Tissues were centrifuged and then triturated in culture media supplemented with 1.5 mg/ml trypsin inhibitor and bovine serum albumin. Cells were cultured in the same media as glioma cell lines and used after they had reached confluence. Some cells were cultured on 12 mm round glass coverslips for staining of glial fibrillary acidic protein (GFAP; Incstar, Stillwater, Minn.).

EXAMPLE 3

Primary Cultures of Rat Astrocytes and Neurons

Hippocampal astrocytes and neurons were prepared from Sprague-Dawley rats (28). Briefly, hippocampi were removed from the decapitated rat pups (P0–P2) and freed of meninges, minced into 1 $mm^3$ pieces and digested in papain solution for 20–30 minutes. Cells were plated in 24-well plates or flasks in MEM supplemented with 10% FBS, 20 mM glucose, 10 U/ml penicillin and 10 $\mu g$/ml streptomycin. Culture media for astrocytic cultures was changed bi-weekly and astrocytes were used after 10 days in culture, at which time >90% of cells were GFAP positive and essentially free of neurons.

For neuronal cultures, culture plates were coated with polyornithine (0.1 mg/ml in 50 mM borate solution (pH 7.6) for 1 hour). As previously demonstrated (28), serum-borne glutamate is excitotoxic to neurons. Thus, astrocytes cultured in 75 $cm^2$ flasks were utilized for preparing glutamate-depleted media (GDM) and neuronal cultures were prepared and maintained in glutamate-depleted media instead of untreated serum-containing media. Cells were plated at a density of 5–10×$10^4$/$cm^2$ for 24 h followed by a 36 h treatment with 15 $\mu M$ cytosine β-D-Arabino-furanoside (Ara-C), which eliminates proliferating cells (mainly astrocytes). Thereafter, neurons received new GDM every 4–5 days. Cultures of 14–25 days were used in vitro and neuronal purity was >90%.

EXAMPLE 4

Glutamate Uptake

Uptake procedures were similar to those described (29), with minor modifications. L-[$^3$H]-glutamate was used as a tracer to study high-affinity, $Na^+$-dependent glutamate uptake. The solution used for uptake experiments consisted of 125 mM NaCl, 3.0 mM KCl, 2.0 mM $CaCl_2$, 1.25 mM $NaH_2PO_4$, 23 mM $NaHCO_3$, 10 mM Glucose, 2.0 mM $MgSO_4$, and was warmed to 37° C. and saturated with 5%/95% $CO_2/O_2$. Cells were washed twice with the uptake solution described above just before experiments commenced. L-[³H]-glutamate was mixed with 5–400 μm glutamate in the uptake solution and the velocity of glutamate uptake was determined over a 5 minute period during which the uptake rate was linear. Glutamate uptake was terminated by three washes with ice-cold uptake solution. Cells were dissolved in 0.3 N NaOH and aliquoted. [³H] activity was detected in a liquid scintillation counter (Beckman Instruments, Fullerton, Calif.). Protein concentration was determined by the Bradford method (30) utilizing a Bio-Rad protein assay kit (Bio-Rad Lab, Hercules, Calif.) and total uptake was normalized to protein content.

EXAMPLE 5

Sampling and Determination of Extracellular and Intracellular Glutamate Levels

Cells were washed twice and incubated in glutamate-depleted culture media with various phenylglycine derivatives for variable periods and the supernatant collected for $[Glu]_o$ measurement. Cells were washed twice with PBS, harvested in 0.3 N NaOH and neutralized with 0.3 N HCl. Aliquots were stored at $-20°$ C. for protein and $[Glu]_i$ determination. Samples containing serum and samples with glutamate levels higher than 20 μM were diluted 1:20–100 with distilled water prior to measurement.

The bioluminescence method was used for detection of glutamate in solution as described by Fosse et al. (31) with minor modifications. Briefly, the glutamate-specific reagent mixture contained 25 mM potassium phosphate (pH 7.0), 40 μg/ml Triton X-100, 100 μM dithiothreitol, 30 μM myristyl aldehyde, 2 mM β-NAD, 250 μM ADP, 2.5 μM FMN, 60 μg/ml luciferase, 300 mU/ml NAD(P)H:FMN oxidoreductase and 0.5 mg/ml glutamate dehydrogenase. 10 μl of samples were transferred to 96 well white cliniplate (Labsystem, Franklin, Mass.). The glutamate-correlated luminescence was measured by a luminescence plate reader equipped with automatic solution pumps capable of delivering defined volumes to individual wells (LUMIstar, BMG LabTechnologies, Durham, N.C.). The reagent mixture was kept on ice, covered with foil during experiments and injected just prior to measurement (80 μl/well). This method can reliably detect glutamate concentrations of >20 nM. It was determined that none of the drugs used in these studies interfered with the bioluminescence assay at the concentration used. Glutamate standards used for calibration were prepared in corresponding glutamate free solutions (For $[Glu]_i$ in 0.15 N NaCl) and measured both at the beginning and at the end of each plate. $[Glu]_i$ was calculated from the amount of intracellular glutamate normalized to total amount of protein and expressed as nmol/mg protein. $[Glu]_o$ was either expressed as absolute concentration (μM) or multiplied by the volume, normalized to cellular protein levels and expressed as nmol/mg protein.

EXAMPLE 6

Ratiometric $[Ca^{2+}]_i$ Measurements

To evaluate the effects of glioma-conditioned media on neuronal $Ca^{2+}$, cultured hippocampal neurons were plated on polyornithine-coated 22×22 mm² glass coverslips. After 14–25 days, cells were loaded in culture media (GDM) for 60 minutes with the ratiometric $Ca^{2+}$ dye Fura-2-acetoxymethylester (10 μM, Teflabs, Austin, Tex.). Subsequently, neurons were rinsed with HEPES buffered saline solution (HBSS) consisting of (in mM): 126.25 NaCl, 3.0 KCl, 2.0 $CaCl_2$, 1.25 $NaH_2PO_4$, 25 HEPES, 10 glucose, 2.0 $MgSO_4$, (pH 7.4). After allowing the dye to de-esterify for 10 minutes in the fresh HBSS, coverslips were placed in a Series 20 Microperfusion chamber (Warner Instruments, Hamden, Conn.) on the stage of a Nikon Diaphot 200 epifluorescence microscope. Neurons were constantly perfused at a speed of 2.0 ml/min with HBSS heated to 37° C. with a TC-344 Dual Heater Controller and a SH-27A in-line heater (Warner Instrument). Glioma-conditioned media was either slowly bubbled with 5%/95% $CO_2/O_2$ or diluted in HBSS. Recordings were obtained with a fluorescent imaging setup (Photon Technology International, Monmouth Junction, N.J.) in which cells were alternately excited at 340 and 380 nm using a monochromatic light source. Emitted light was collected at >520 nm using a Hamamatsu intensified CCD camera. Images were digitized online and 340/380 nm ratios obtained every 10 s. The 340/380 nm ratio was converted to absolute $[Ca^{2+}]_i$ by the equation:

$$[Ca^{2+}]_i = Kd \times Sf2/Sb2 \times (R-R_{min})/(R_{max}-R) \quad (32).$$

$R_{max}$ and $R_{min}$ were experimentally determined (33).

To study the effects of glioma cells on neurons, a modified time-lapse video-microscopy system was utilized in which neurons, cultured on 35 mm petri dishes with a glass bottom (MatTek, Ashland, Mass.), were loaded with Fura-PE3, and placed in a Leiden chamber (34) mounted on top of a Nikon Diaphot microscope. The Leiden chamber was maintained in a humidified environment at 37° C., supplied with $H_2O$ saturated 5%/95% $CO_2$/air mixture through the gas duct of the chamber. Changes in osmolarity of the medium were <5% after 48 h (28). Cells were alternately excited at 340 and 380 nm through a Lambda 10-2 filter wheel driver (Sutter Instrument, Novato, Calif.) controlled by Axon Imaging Workbench 2.1 (Axon Instrument, Foster city, Calif.). Emitted light was collected at >520 nm using an intensified CCD camera and images were digitized and ratios obtained every 30 s. These were again converted to absolute value of $[Ca^{2+}]_i$ using the equation described above. All media changes and reagent applications were made through two sterile perfusion tubes. Fresh glioma-conditioned media was either directly applied to the cultured neurons or diluted with glutamate-depleted media prior to application. All tested reagents were also prepared in glutamate-depleted media to the final concentration and equilibrated with $CO_2$ and temperature for at least one hour in the incubator prior to application. Glioma cells were detached from 10 cm petri dishes with trypsin and suspended in glutamate-depleted media, centrifuged and resuspended in fresh glutamate-depleted media at a density of $1.0 \times 10^6$/ml. The time delay between final suspension of glioma cells and the application to neurons was approximately 1 min.

EXAMPLE 7

Assaying Excitotoxic Effects of Glioma Cells to Neurons

To assess the effects of glioma cells on the survival of neurons, three sets of experiments were performed:

(A) To ascertain potential excitotoxicity of glioma-conditioned media (GCM), glutamate-depleted media (GDM) was conditioned in glioma cultures for 6–24 h. The resulting glioma-conditioned media was applied to neurons with the identical batch of glutamate-depleted media used as control. Neuronal survival was determined by trypan blue exclusion.

(B) For co-culturing of neurons and glioma cells, glioma cells were harvested from a culture flask or 6 well plate with trypsin, spun down, washed and resuspended in glutamate-depleted media. Glioma cells were applied to neuronal cultures at a density of $1 \times 10^5/cm^2$ where they settled down within an hour and formed direct contact with neurons. Neurons could be readily distinguished from glioma cells by their long tapered processes and round cell bodies. Surviving neurons excluding trypan blue were counted 40 h after co-culturing.

(C) For co-culturing of neurons and glioma cells without direct contact, glioma cells were cultured on $22 \times 22$ mm$^2$ glass coverslips with wax spots on each corner. Once the cultures had reached confluence, the coverslips were placed up-side down on top of neurons cultured in 6-well plates with glioma cells facing the neurons but separated by the wax spots as spacers with approximately 1 mm clearance. In all experiments, neuronal death was determined by determining the ratio of trypan blue-excluding, healthy cells and typhan blue-containing dead cells after 35–40 h co-culture. For each experiment, at least 3–6 wells of neurons, each with 6–8 randomly selected fields, were examined.

EXAMPLE 8

Statistics

All data were expressed as mean±standard error. Control values were derived from untreated sister cultures. Statistical evaluations of the data were performed using t test or analysis of variance (ANOVA) as appropriate. Significance levels were: * $P<0.05$,  $P<0.01$, * $P<0.001$.

EXAMPLE 9

Glioma Cells Show Compromised Glutamate Transport

Figure 1A:
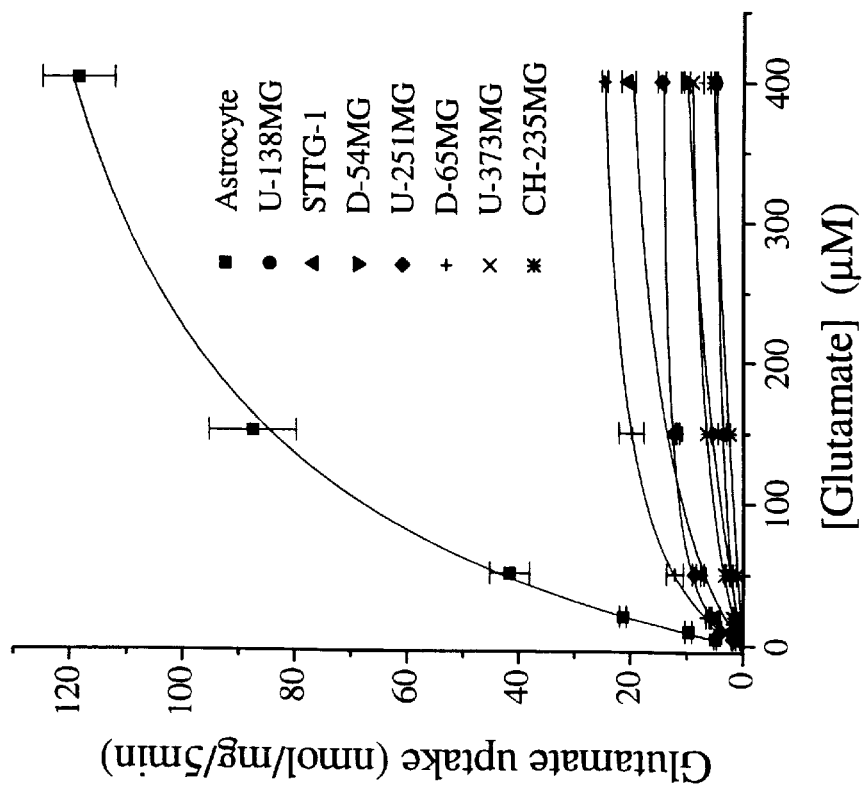
FIG. 1A: Glutamate uptake was determined over a period of 5 min with $[Glu]_o$ ranging from 5 to 400 $\mu$M mixed with 0.4 $\mu$Ci/ml $^3$H-glutamate. Primary astrocyte cultures were prepared from P0 rat hippocampal (35DIV). Glioma cell lines used are listed in the legend. Each point is the mean±SE and n=4.

The uptake of glutamate from the extracellular environment was studied by assessing Na$^+$-dependent influx of glutamate. These studies included glioma cells isolated from 5 surgically removed human glioma tissues, 7 commonly studied glioma cell lines, and for comparison, normal rat astrocytes. As summarized in FIG. 1A, the rate of glutamate uptake into glioma cell lines and normal astrocytes were assessed over a range of glutamate concentrations of 5 to 400 μM. At every glutamate concentration tested, the rates of glioma glutamate uptake were remarkably lower than that of normal astrocytes. The mean value of glutamate uptake (at a concentration of 50 μM) for glioma cells lines (7 different lines) and primary human glioma cultures (5 different glioblastoma multiforme) were averaged and plotted along with glutamate uptake of normal astrocytes in FIG. 1B. These data show an approximately 10-fold difference in glutamate uptake between normal astrocytes and glioma cells. The uptake rates determined in the control rat primary astrocytes are close to those reported for normal human astrocytes (35), thus eliminating the possiblity that species differences may account for the large decrease in glioma cell uptake. Determination of the $V_{max}$ and $K_m$ values for glutamate uptake suggest that the observed difference was due mainly to a >20 fold reduction in the $V_{max}$ of glutamate uptake into glioma cells.

EXAMPLE 10

Figure 2A:
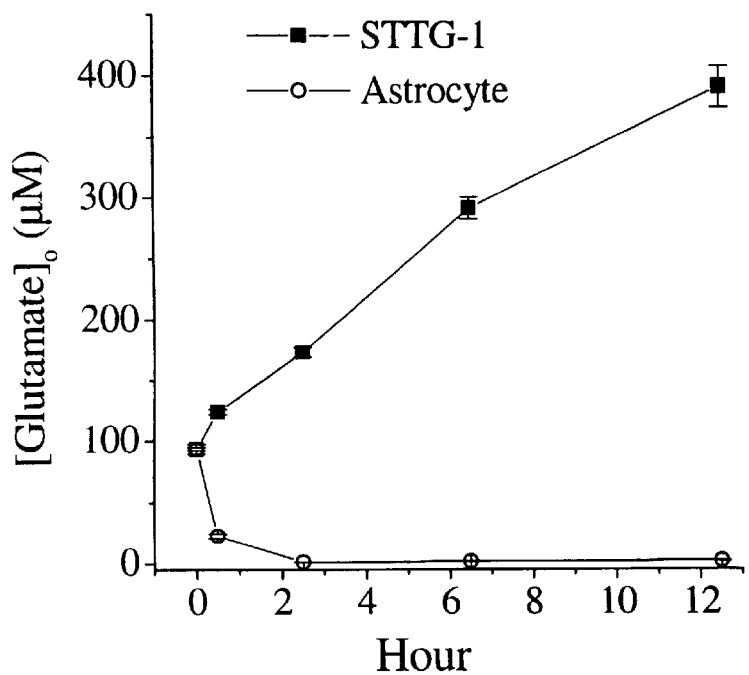
FIG. 2A: Astrocytes depleted serum glutamate levels from 92 $\mu$M to 1 $\mu$M within 3 hours, whereas STTG-1 glioma cells induced a 3-fold increase of glutamate concentration in the media after a 12 h incubation.

Glioma Cells Release Neurotoxic Concentrations of Glutamate into the Culture Media As was reported (28), astrocytes can effectively deplete glutamate from serum-containing media, thereby promoting the survival of neurons. This is most likely a key factor in maintaining extracellular glutamate concentrations ($[Glu]_o$) in the brain below neurotoxic concentrations at ~1 μM. In light of the above findings, it was investigated whether the reduced glutamate transport rates in glioma cells would also lead to compromised capability in maintaining low $[Glu]_o$. Therefore, $[Glu]_o$ was monitored in cultured glioma cells with fresh culture media as compared to normal astrocytes. As previously reported, astrocytes depleted serum containing glutamate (~92 μM) within 3 h and reduced $[Glu]_o$ to ~1 μM. Surprisingly, glioma cells did not reduce the glutamate content in the media, but instead, $[Glu]_o$ in glioma cultures increased 3 fold over a 12 h period (FIG. 2A).

Figure 2B:
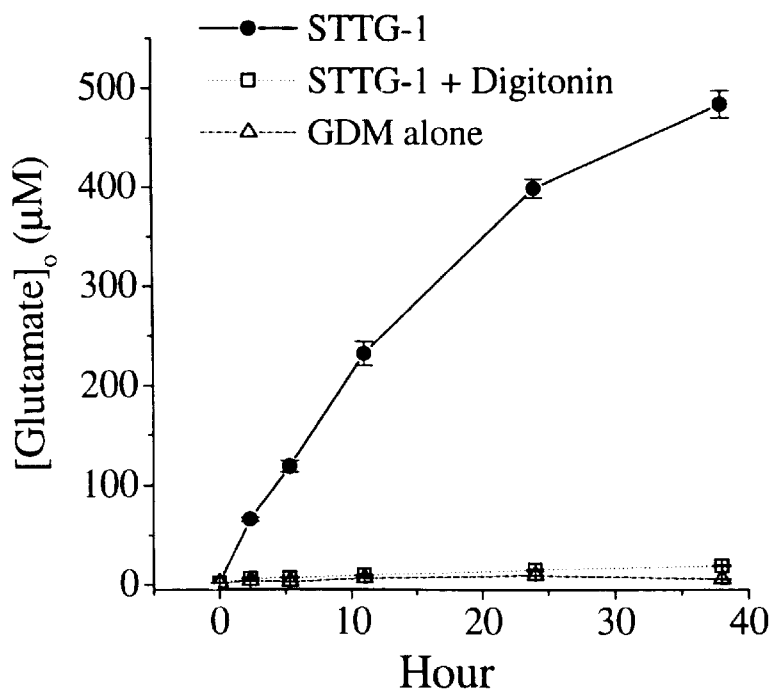
FIG. 2B: STTG-1 glioma cells induced $[Glu]_o$ elevation in glutamate-depleted media (GDM), whereas cells disintegrated by digitonin (0.1%) or GDM alone resulted in only small increases in $[Glu]_o$. Other glioma cell lines induced similar $[Glu]_o$ elevations.

Since this increase must have been due to glutamate release from glioma cells, this was assessed more quantitatively by placing glioma cultures into media in which glutamate had been previously depleted by 4–6 hours pre-incubation with hippocampal astrocytes. This glutamate-depleted media (GDM) contained glutamate concentrations of ~1 μM. Glioma cells very rapidly elevated $[Glu]_o$ and within 5 hours, $[Glu]_o$ exceeded 100 μM (FIG. 2B).

To evaluate the possibility that the glutamate was spontaneously generated from precursor molecules like glutamine by enzymes released from glioma cells, $[Glu]_o$ was also monitored in cell free glutamate-depleted media or in glutamate-depleted media with cells disintegrated by 0.1% digitonin (36). $[Glu]_o$ only marginally increased under those conditions (FIG. 2B, dotted lines). The elevation of $[Glu]_o$ in glioma culture was almost linear during the first 10 h. The velocity of glutamate release could thus be expressed as the amount of glutamate released into the media (0.5 ml) normalized for cell protein. This yielded a value of 4.94 nmol/min/mg protein for glioma cells, a value 44-fold higher than the glutamate generated by disintegrated cells (0.11 nmol/min/mg, among which, 30% may come from glutamate-depleted media alone and 70% was accounted for by the released enzymes). These data confirmed that the increases in $[Glu]_o$ were due to release from glioma cells rather than glutamate synthesized in the media. Similar to the $[Glu]_o$ elevations in STTG-1 cells, $[Glu]_o$ increases ranging from 102.2±15.2 μM to 597.3±23.6 μM were observed in the other six glioma cell lines tested, with an average of 388.97±76.56 μM in a period of 48 hours. In primary glioma cultures from brain tumor tissues, $[Glu]_o$ ranged from 86.3±10.2 to 733.7±8.3 μM.

Figure 2C:
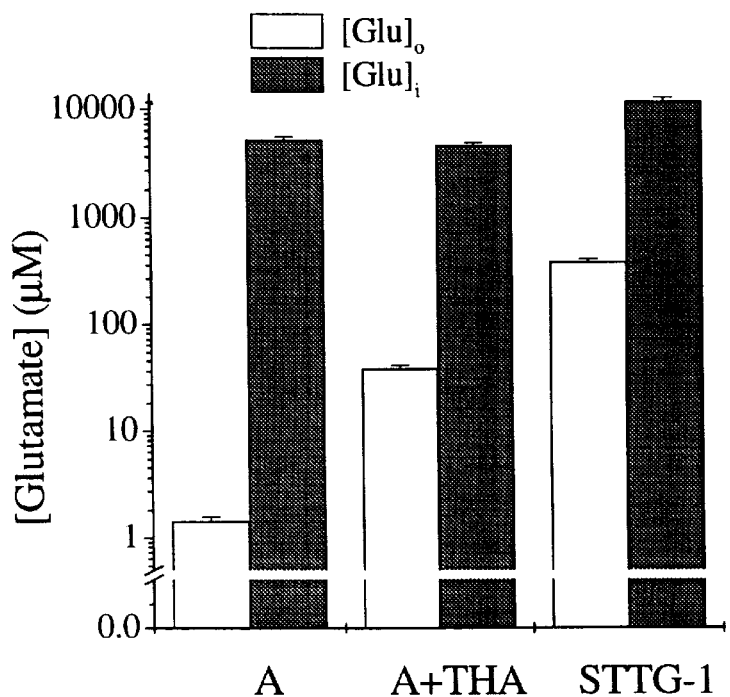
FIG. 2C: The glutamate transport inhibitor threohydroxyaspartate (THA, 1 mM for 70 min) in GDM significantly increased $[Glu]_o$ in astrocyte cultures (A+THA) as compared to astrocytes in GDM alone, but without significant changes in $[Glu]_i$. After 38 hours in GDM, $[Glu]_o$ in STTG-1 cell cultures reached levels of ~0.5 mM, but $[Glu]_i$ remained at 10 mM.
Figure 2D:
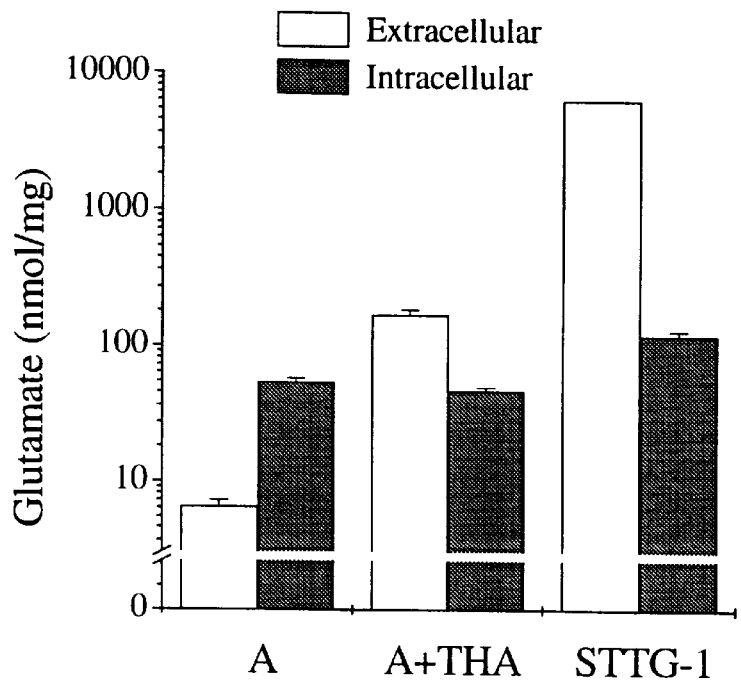
FIG. 2D: The same conditions were used as in FIG. 2C, but the total amount of glutamate released into the media was compared to the intracellular glutamate content. In all cases, released glutamate from THA treated astrocytes or glioma cells greatly exceed the intracellular content (mean±SE, n=6).

In good agreement with the literature (37), blocking glutamate uptake of astrocytes with the glutamate transport inhibitor threo-hydroxyaspartate (THA) also resulted in marked elevations of $[Glu]_o$. By calculating the $[Glu]_i$ from the amount of intracellular glutamate and protein content (1 mg protein in ~10 μl of cell volume), both $[Glu]_o$ and $[Glu]_i$ of control astrocytes, astrocytes treated with THA (1 mM for 70 min) and glioma cells (STTG-1, 38 h after changing to GDM) were plotted in FIG. 2D. THA did not significantly change intracellular $[Glu]_i$ in astrocytes, similarly, even after $[Glu]_o$ in glioma cultures had reached levels close to 0.5 mM, glioma cells maintained $[Glu]_i$ of ~10 mM. Indeed, this transmembrane glutamate gradient must have fueled the elevation of $[Glu]_o$. However, in these in vitro culture systems, the extracellular fluid volume exceeds the cell volume by ~1000-fold. The total amount of released glutamate must thus be substantially higher. In FIG. 2D, the total amount of glutamate released into the media were compared with the intracellular glutamate content in astrocytes and glioma cultures shown in FIG. 2C. In THA-treated astrocytes or glioma cells, the amount of glutamate released into the media exceeded the intracellular glutamate content by a factor of 3.6 and 52.3, respectively. This can only be explained by continuous synthesis of glutamate by these cells to compensate for the constant glutamate release. These data suggest that driven by the transmembrane glutamate gradient, the absence of sufficient uptake capability make glioma cells a source of glutamate to be released.

EXAMPLE 11

Glutamate Release from Glioma Cells can be Inhibited by Phenylglycine Derivatives It was recently found that several compounds that had been previously characterized to have either stimulatory or inhibitory effects on metabotropic glutamate receptors can reduce $[Glu]_o$ in astrocytic cultures, however, their effects on $[Glu]_o$ do not involve metabotropic glutamate receptors (38). Among the various compounds tested, S-4CPG was the most effective. The effects of S-4CPG on glutamate release from glioma cells were therefore tested.

Figure 3B:
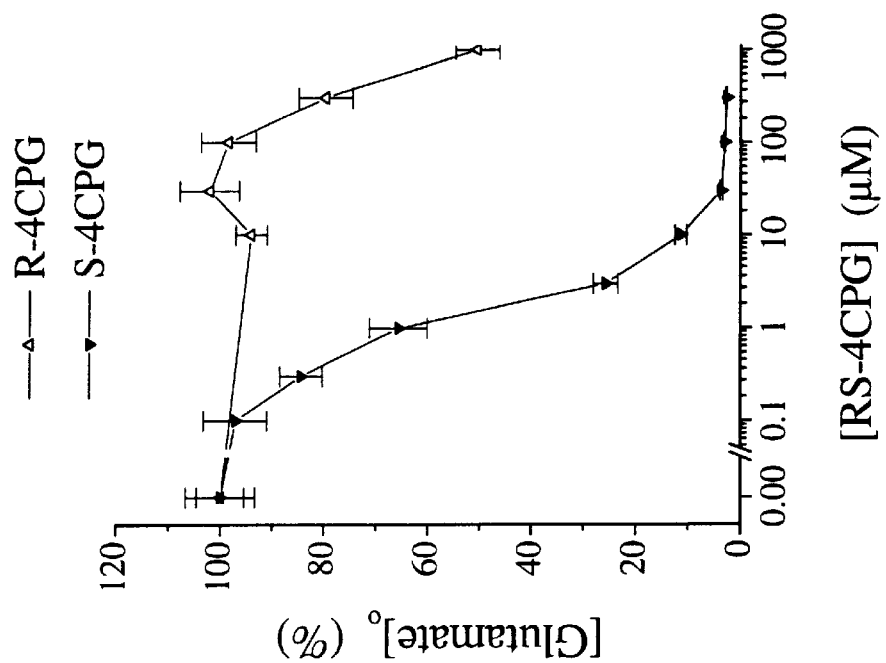
FIG. 3B: R-4CPG is 1000-fold less effective than S-4CPG in reducing $[Glu]_o$ as measured after a 24 h treatment.
Figure 3A:
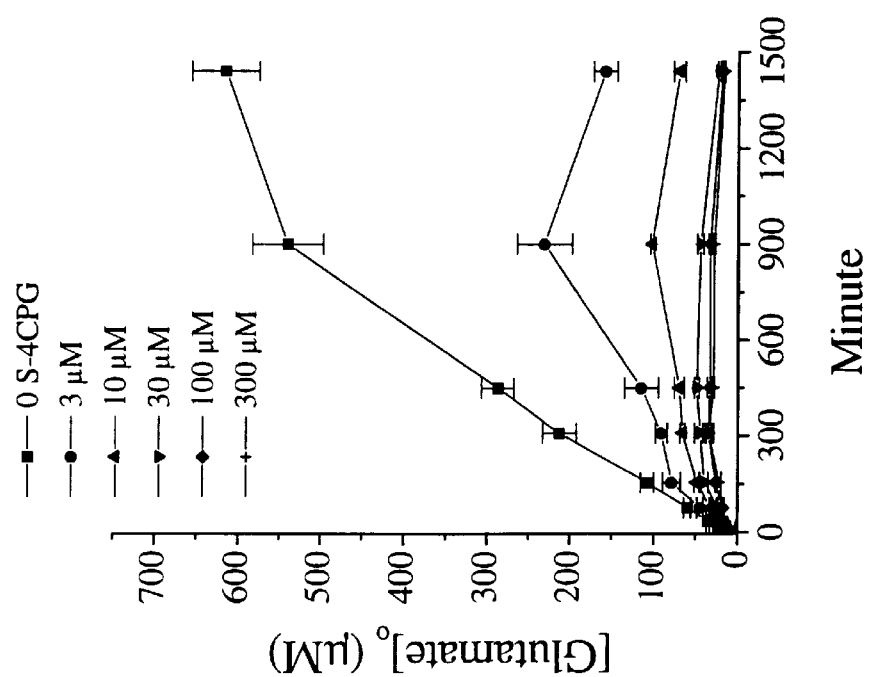
FIG. 3A: S-4CPG dose dependently reduced $[Glu]_o$ when STTG-1 cells were cultured in GDM.
Figure 3C:
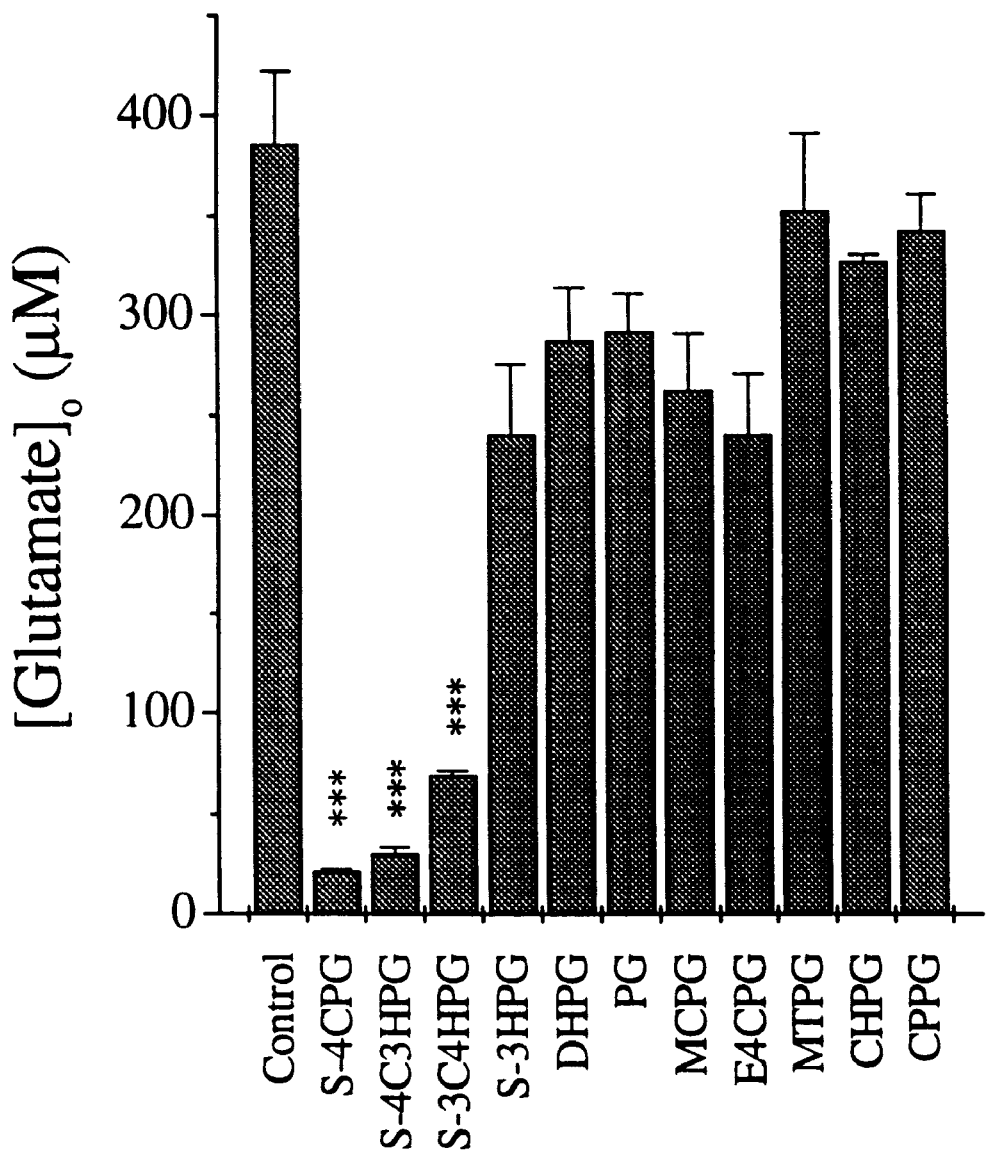
FIG. 3C: Effects of different phenylglycine derivatives (100 $\mu$M) in modulating $[Glu]_o$ in STTG-1 glioma cultures was assessed after a 24 h incubation (n=4, mean±SE, *** $P<0.001$ by ANOVA).

Glioma cells were incubated in GDM medium with S-4CPG at concentrations ranging from 3 to 300 $\mu$M and $[Glu]_o$ was sampled over a period of 24 h (FIG. 3A). S-4CPG markedly and dose-dependently reduced the elevations of $[Glu]_o$, with an apparent $EC_{50}$ of 1–2 $\mu$M. At 24 h, 100 $\mu$M S-4CPG reduced $[Glu]_o$ from 616.0±40.9 $\mu$M to 18.8±0.6 $\mu$M (n=4) with a 32-fold reduction. The effect of (S,R)-4-carboxyphenylglycine was stereospecific as the R-4CPG isomer was 1000-fold less potent (FIG. 3B). Other structurally related phenylglycine derivatives were also tested. Most of them were previously characterized as mGluR agonists or antagonists, although their function on $[Glu]_o$ do not involve mGluR. Among the tested reagents, S-4CPG showed the highest efficiency, followed by S-4C3HPG and S-3C4HPG. It appears that the presence of a carboxyl group in the phenyl ring dramatically increases the efficiency (e.g. S-4CPG, S-4C3H-PG, S-3C4HPG vs. PG, S-3HPG and DHPG), whereas replacing the hydrogen that is attached to the α-carbon with a larger group dramatically reduced the efficiency (e.g. MCPG, E4CPG).

EXAMPLE 12

Figures 4A, 4B:
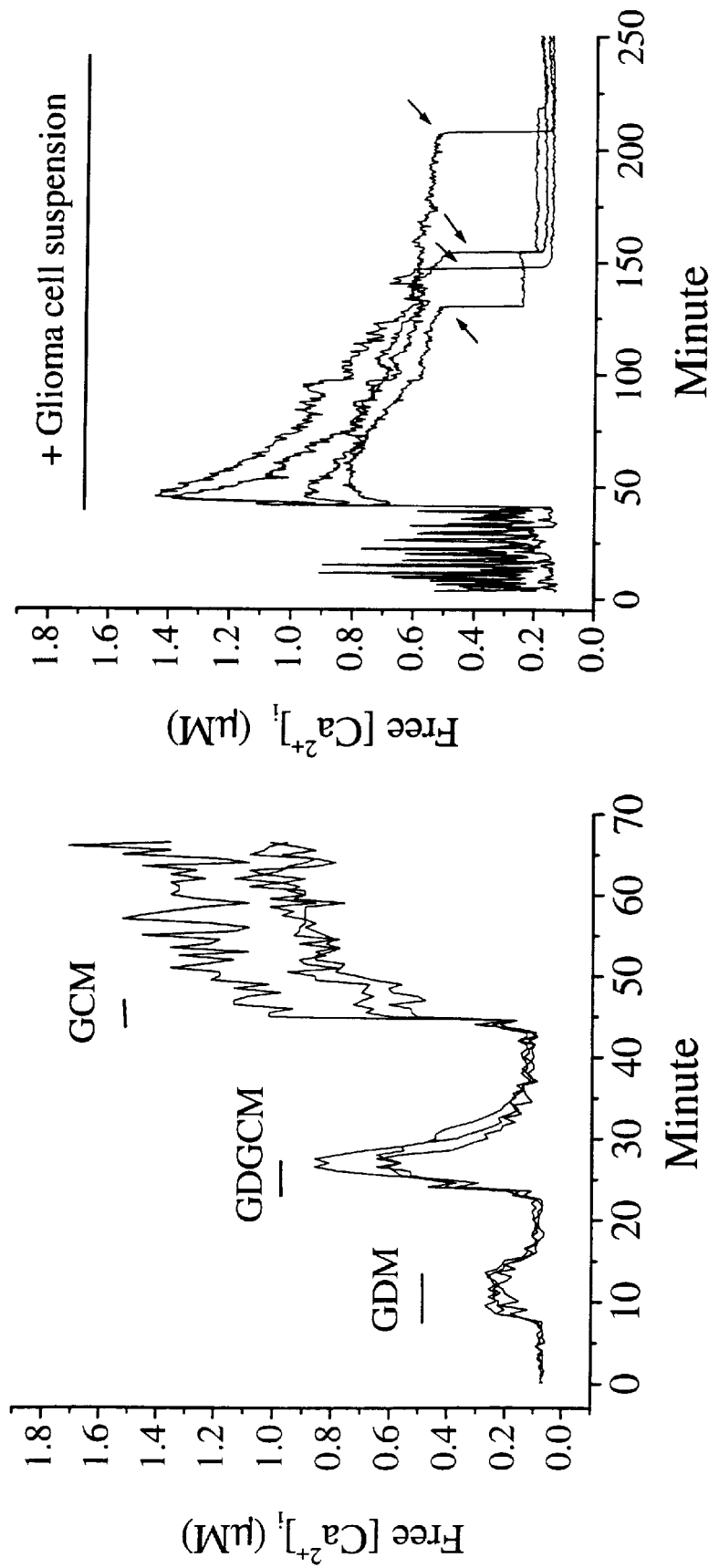
FIG. 4A: Hippocampal neurons (14DIV) in HBSS responded to glutamate-depleted media (GDM) with a transient $[Ca^{2+}]_i$ increase, but a 3 minute perfusion with glioma-conditioned media (GCM, conditioned by STTG-1 cells for 8 hours) elicited a sustained $[Ca^{2+}]_i$ elevation. 5 minute application of GDGCM (glutamate-depleted GCM, conditioned by normal astrocytes to deplete glutamate) only triggered smaller and transient $[Ca^{2+}]_i$ rises.
FIG. 4B: Hippocampal neurons cultured in GDM exhibit spontaneous $[Ca^{2+}]_i$ oscillations. Addition of glioma cells (STTG-1) suspended in GDM induced a large sustained $[Ca^{2+}]_i$ elevation followed by membrane disintegration (arrows).

Co-culture of Hippocampal Neurons with Glioma Cells or Glioma-conditioned Medium Elicits Large Calcium Responses in Neurons Activation of glutamate receptors commonly leads to elevations of $[Ca^{2+}]_i$ in neurons (39,40), and prolonged exposure to glutamate can induce $Ca^{2+}$-dependent neurotoxicity (1,41). Therefore, glutamate released by glioma cells would have the capacity to trigger a calcium response in neurons in the proximity of glioma cells. To demonstrate this, cultured hippocampal neurons were first exposed briefly to glioma-conditioned media. As shown in FIG. 4A, a switch from HEPES buffered solution to glutamate-depleted media (~1 $\mu$M glutamate) elicited only a small calcium response which immediately returned to basal line after removal of the glutamate-depleted media. This calcium response was likely caused by the residual glutamate and serum factors, including growth factors and lysophosphatidic acid (33) contained in this medium. Subsequently, hippocampal neurons were exposed to a glioma-conditioned medium that had subsequently been conditioned for 6 h by primary hippocampal astrocytes in order to deplete glutamate. This glutamate-depleted glioma-conditioned media (GDGCM) also elicited a reversible $[Ca^{2+}]_i$ response of larger amplitude than observed with astrocyte-conditioned medium. Lastly, these neurons were exposed for 3 min to glioma-conditioned medium (GCM) in which glutamate was not pre-depleted. This led to a large and persistent increase in $[Ca^{2+}]_i$ from which the cells did not recover (FIG. 4A). This $Ca^{2+}$ increase must have been caused by a molecule secreted into the medium by glioma cells, most likely glutamate. These experiments were repeated with a variety of glioma cell lines and primary glioma cells cultured from patient brain tumor tissues, with all yielding similar results.

Figures 4C, 4D:
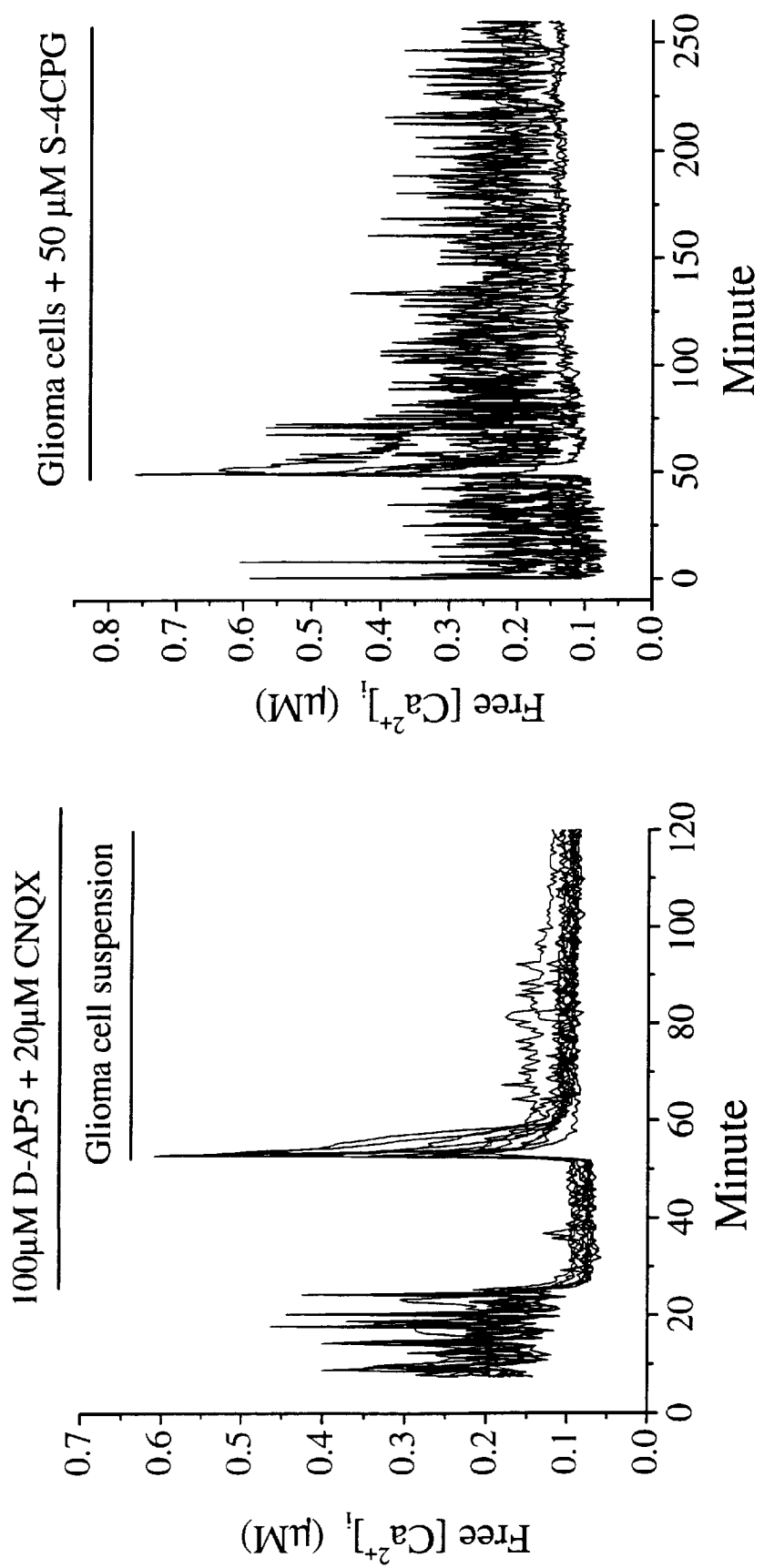
FIG. 4C: D-AP5 and CNQX inhibited the spontaneous $[Ca^{2+}]_i$ oscillations and blocked the sustained $[Ca^{2+}]_i$ elevation by glioma cells.
FIG. 4D: Glioma cells (STTG-1) pretreated and in the continuous presence of S-4CPG did not induced significant $[Ca^{2+}]_i$ elevation in hippocampal neurons.

By using the combination of time-lapse video microscopy and ratiometric calcium imaging, the calcium response of neurons to direct application of glioma cells freshly dispensed in glutamate-depleted media was also studied. Cultured hippocampal neurons maintained in vitro for 2 weeks were imaged on the stage of a microscope and incubated with fresh glutamate-depleted media which did not induce any sustained $[Ca^{2+}]_i$ increases. However, these network forming neurons displayed spontaneous $[Ca^{2+}]_i$ oscillations as previoulsy reported (42,43). Superfusion of a cell suspension of STTG-1 glioma cells onto neuronal cultures elicited a large sustained calcium response in neurons (FIG. 4B). Neurons did not recover from these large $Ca^{2+}$ increases but instead began to die after a variable delay of 90–150 minutes. This is evident by abrupt drops of the ratiometric signal (arrows in FIG. 4B), indicating the disruption of plasma membrane and leakage of calcium dye out of the cells. Both the spontaneous $Ca^{2+}$ oscillations and the glioma cell induced $[Ca^{2+}]_i$ rises could be blocked if 100 $\mu$M D-AP5 and 20 $\mu$M CNQX were included in the media (FIG. 4C). Similar $[Ca^{2+}]_i$ elevations were observed when using other glioma cell lines or biopsy derived glioma cells. Treatment with D-AP5 and CNQX also completely prevented neurotoxicity, suggesting that the glioma cell-induced neuronal $Ca^{2+}$ response was due to the activation of glutamate receptors on neurons.

Since S-4CPG was found to profoundly reduced glutamate efflux from glioma cells (FIG. 3A), pre-treatment of glioma cells with S-4CPG was examined to determine if pre-treatment could reduce their ability to elicit excitotoxicity. As shown in FIG. 4D, exposure of hippocampal neurons to a cell suspension of glioma cells pre-treated for 6 h prior to, and in the continued presence of, 50 $\mu$M S-4CPG did not induce any sustained rises in neuronal $[Ca^{2+}]_i$. This is consistent with the fact that glutamate release from glioma cells could be inhibited by S-4CPG. When exogenous glutamate was applied to neurons as a control, no difference in the neuronal $[Ca^{2+}]_i$ response was introduced by the presence or absence of 50 $\mu$M S-4CPG. These results suggest that the absence of a $[Ca^{2+}]_i$ response in S-4CPG treated glioma cells is due to the suppression of glutamate release from glioma cells.

EXAMPLE 13

Figure 5B:
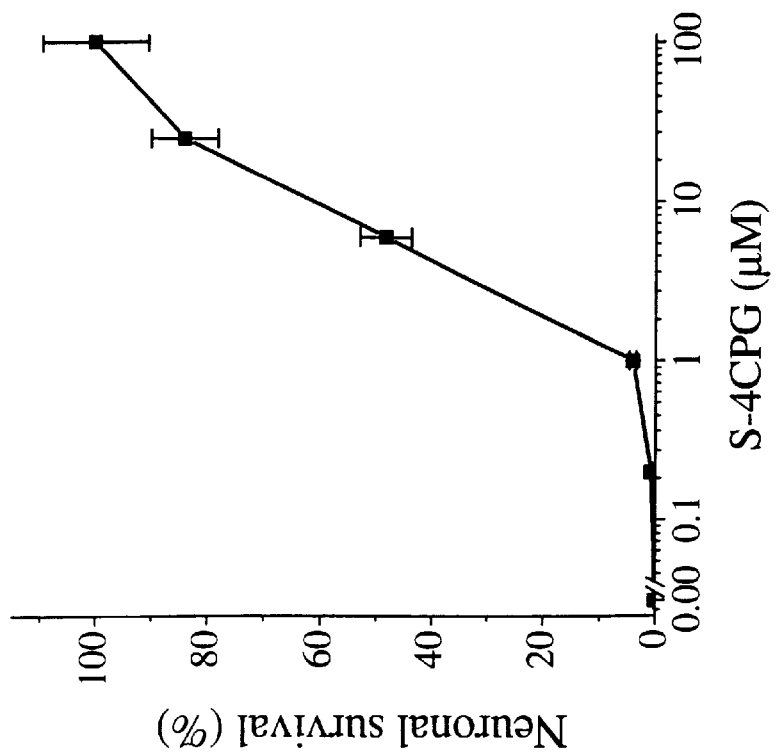
FIG. 5B: The presence of S-4CPG yielded dose-dependent neuronal protection. GCM (8 hours incubation of GDM in STTG-1 cell cultures with various S-4CPG concentrations) was freshly transfered to neuronal cultures and viable neurons counted after 16 hours.
Figure 5A:
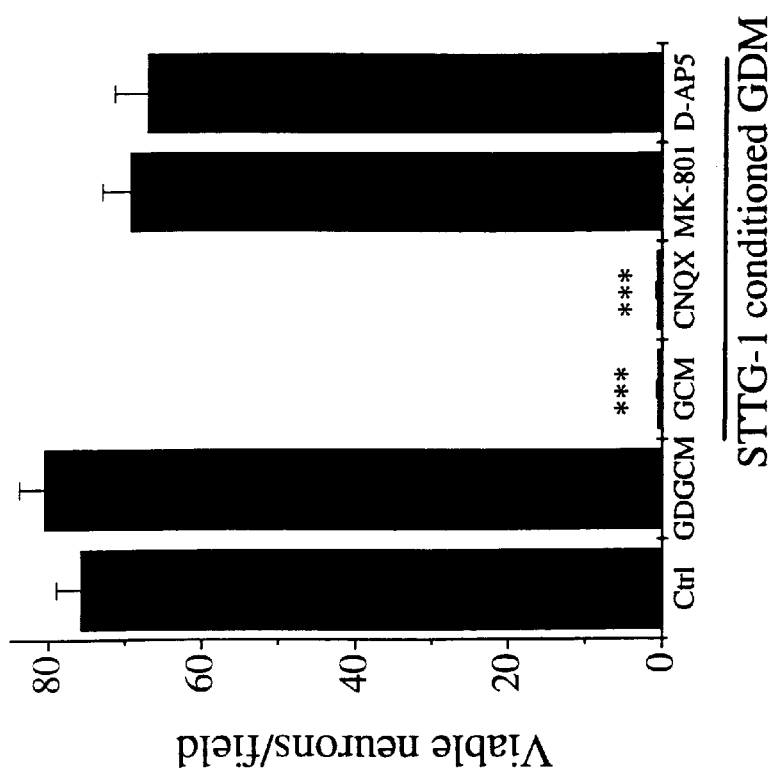
FIG. 5A: STTG-1-conditioned GDM (GCM) induced a near complete loss of cultured hippocampal neurons. This was blocked by the NMDA receptor antagonist, MK-801 (10 $\mu$M) or D-AP5 (50 $\mu$M). The glutamate-depleted GCM (GDGCM) prepared by incubating the GCM with astrocytes for 8 hours had no toxic effects. (mean±SE, n=15–36 random fields, *** $P<0.001$ by ANOVA).

Glioma Cells Kill Neurons Through a Toxic Release of Glutamate Which Can be Prevented by Phenylglycine Derivatives Loss of intracellular $Ca^{2+}$ homeostasis and sustained elevations of $[Ca^{2+}]_i$ has been demonstrated to be a common pathway in excitotoxic neuronal death (1,23). The ability of glioma cells and glioma-conditioned medium to induce excitotoxicity in hippocampal neurons was assessed in vitro. Cultured hippocampal neurons were incubated for 16 h in glioma-conditioned media (glioma-conditioned media, prepared by incubating GDM with STTG-1 for 5 h) in the presence or absence of several glutamate receptor blockers (FIG. 5A). The percentage of viable neurons was determined by trypan blue exclusion and treated cells were compared to neurons received a media change with fresh GDM.

Application of glioma-conditioned media essentially wiped out the entire neuronal cell population. Neuronal loss was inhibited by >95% in the presence of the NMDA antagonists MK-801 (10 $\mu$M) or D-AP5 (50 $\mu$M). The KA/AMPA receptor antagonist CNQX (20 $\mu$M) was without effect, suggesting that the toxicity of glioma-conditioned medium was primarily caused by activation of neuronal NMDA receptors. If glutamate-depleted glioma-conditioned media (GDGCM) was used, prepared by a 6 h incubation of glioma-conditioned media with primary hippocampal astrocytes to deplete glutamate (28), neurotoxicity was completely removed (FIG. 5A).

Since it was shown that S-4CPG greatly reduced glutamate release from STTG-1 glioma cells (FIG. 3A), the effects of S-4CPG on the excitotoxicity induced by glioma-conditioned media was also tested. STTG-1 cells were incubated in glutamate-depleted media for 8 h with S-4CPG at different concentrations. Subsequently, the medium was harvested and applied to neurons and neuronal survival was assessed 16 h later. The results (FIG. 5B) show a dose-dependent protective effect of S-4CPG that is comparable to the dose-dependent inhibition of glutamate release from glioma cells by this compound.

Figure 6A:
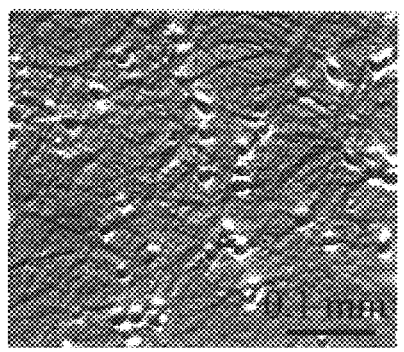
FIG. 6A: Untreated hippocampal neurons at 2 weeks in vitro.
Figure 6B:
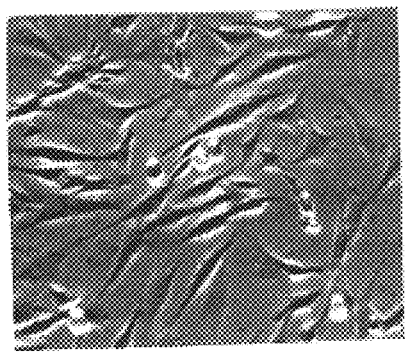
FIG. 6B: Typical STTG-1 glioma cells in culture.
Figure 6C:
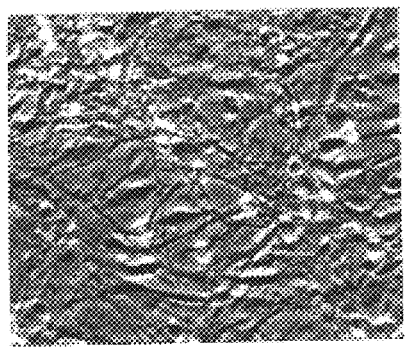
FIG. 6C: 40 hours after applying STTG-1 glioma cell suspension to neuronal cultures, damage to the neurons was observed.
Figure 6D:
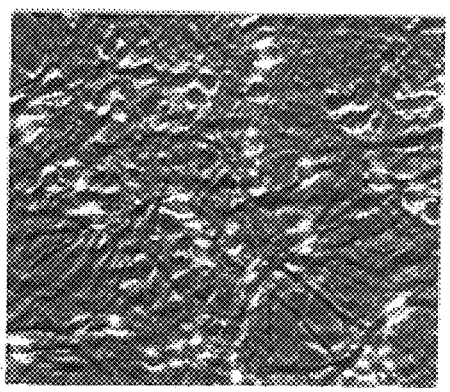
FIGS. 6D, E: 10 $\mu$M MK-801 or 50 $\mu$M D-AP5 treatment, respectively, protected neurons.
Figure 6E:
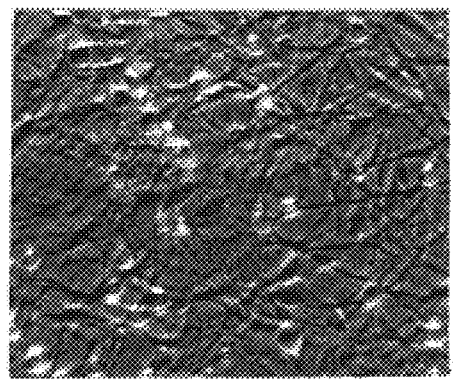
FIG. 6 shows excitotoxicity in glioma-neuronal co-cultures.
FIG. 6F: Trypan blue excluded, process-bearing neurons were counted 40 h after co-culturing with STTG-1 glioma cells. Co-culturing induced a 70% neuronal death, that was largely protected by the NMDA receptor antagonits, MK801 or D-AP5 (mean±SE, n=15–24 random fields, ** $P<0.01$ by ANOVA, bar=100 $\mu$m).
Figure 6F:
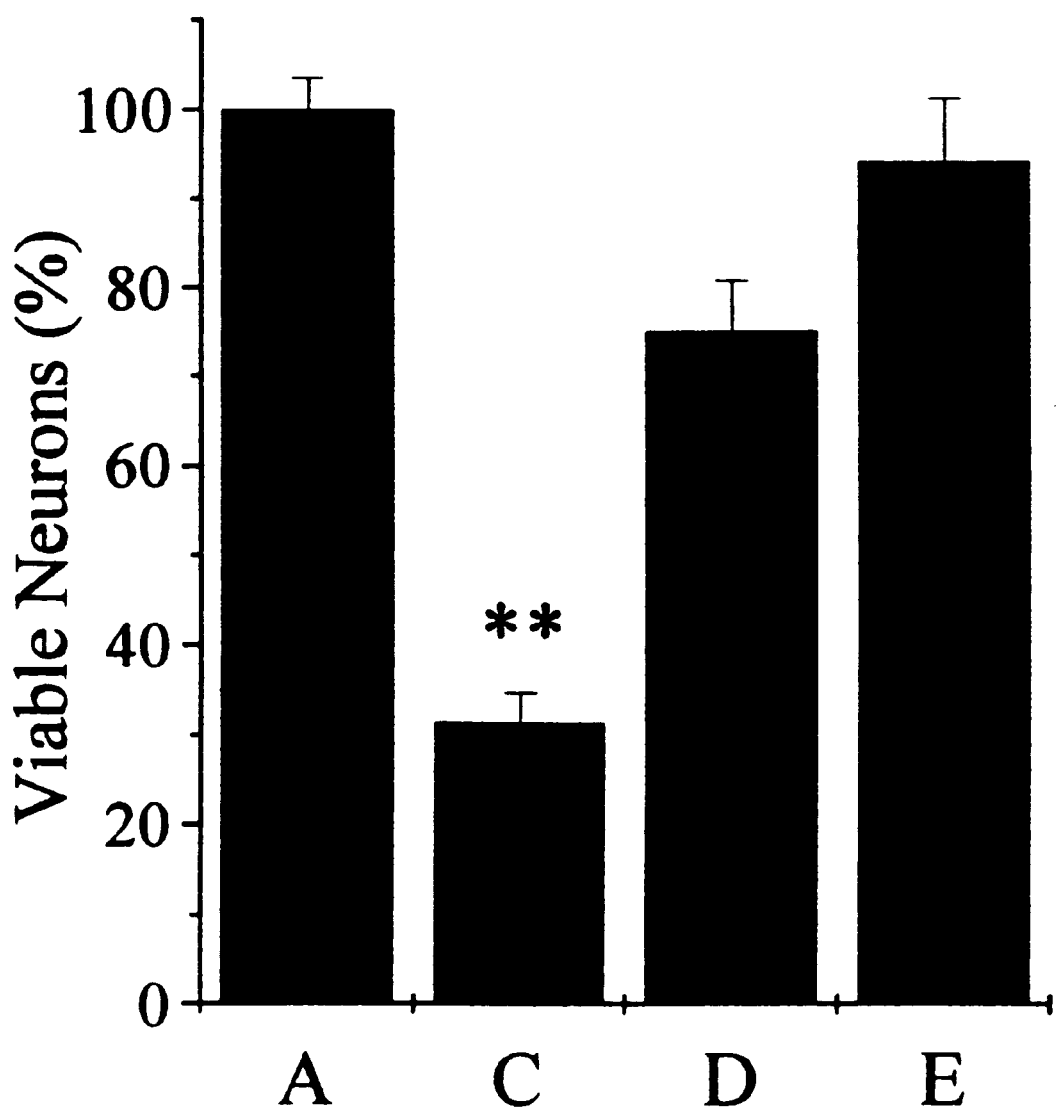

To more closely mimic conditions that neurons in the proximity of a glioma may encounter in vivo, several glioma-neuronal co-culture experiments were performed in which cells were either in direct contact with each other (FIG. 6) or where neurons and glioma cells were in close apposition but without physical contact (FIG. 7). For direct co-culture experiments, STTG-1 cells ($1 \times 10^5$/well) were suspended in GDM and plated onto neuronal cultures. Within 40 hours after the application of glioma cells, substantial neuronal death was observed (FIG. 6B) with approximately a 70% loss in viability (FIG. 6F). Again, this toxicity could be largely prevented by addition of 10 $\mu$M MK-801 or 50 $\mu$M D-AP5 to the media (FIG. 6, panels D and E).

Figure 7A:
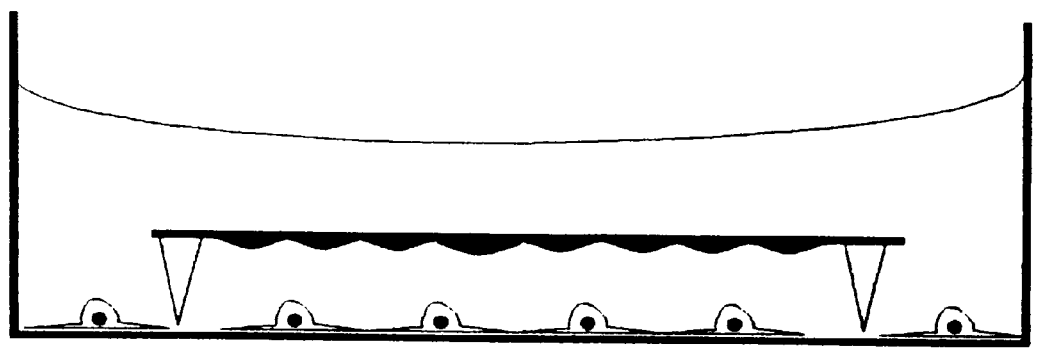
FIG. 7A: A schematic diagram of STTG-1 cells cultured on 22×22 mm glass coverslips with wax spots placed in each corner as spacers. Once the cells had reached confluence, the coverslips were transferred to 6-well plates previously cultured with hippocampal neurons.
Figure 7B:
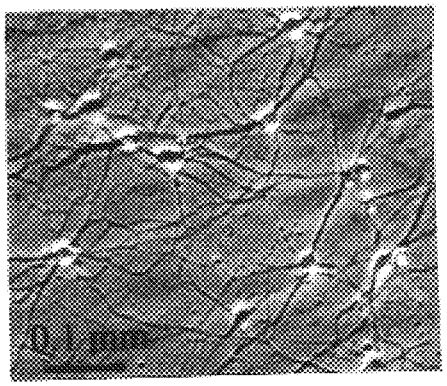
FIG. 7B: Hippocampal neurons alone (18 DIV).
Figure 7C:
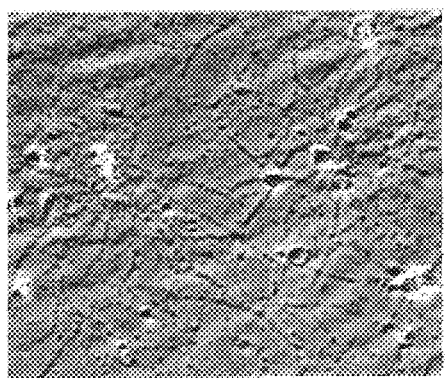
FIG. 7C: Disintegrated neurons in the area underneath glioma coverslips 36 h after co-culturing.
Figure 7D:
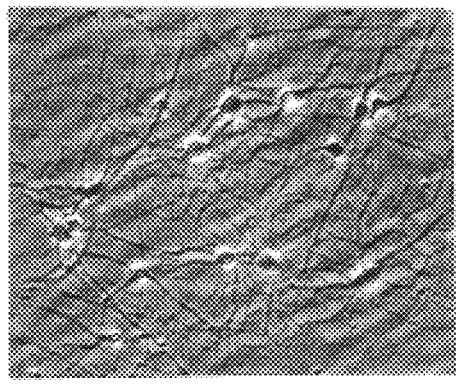
FIG. 7D: Same as panel C, but neurons were protected when the STTG-1 were pre-treated 7 h prior to co-culture and in the continuos presence of 10 $\mu$M S-4CPG in the culture media.
Figure 7F:
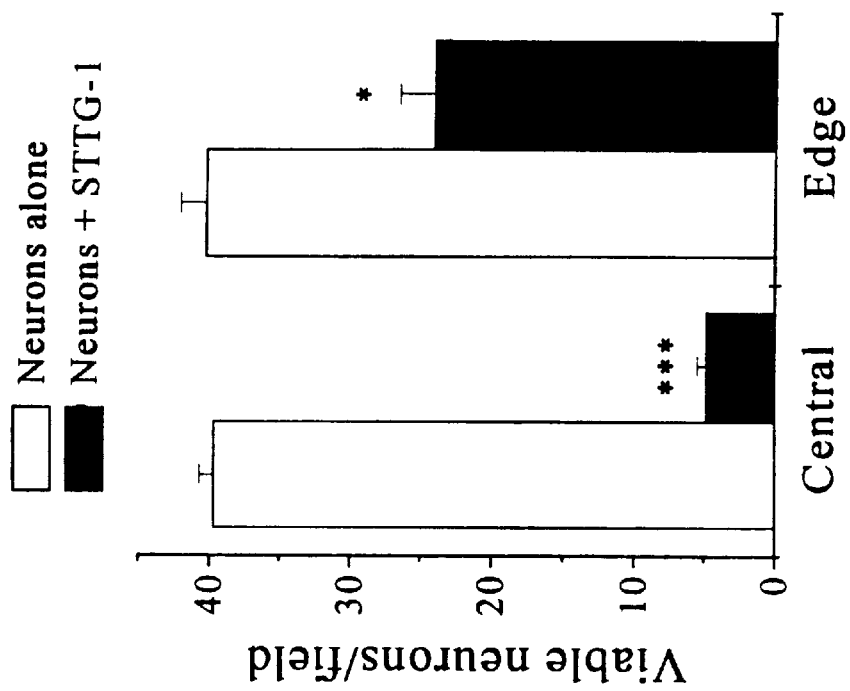
FIG. 7F: Neurons on the edge of the well that were beyond the coverslips remained more viable than those directly under the glioma cells. (Each bar represents the mean±SE of 24–36 random fields counted from 3 separate wells, panel F pooled from two experiments. * $P<0.05$, *** $P<0.001$ by ANOVA for panel E and t-test for panel F, bar=100 $\mu$m).
Figure 7E:
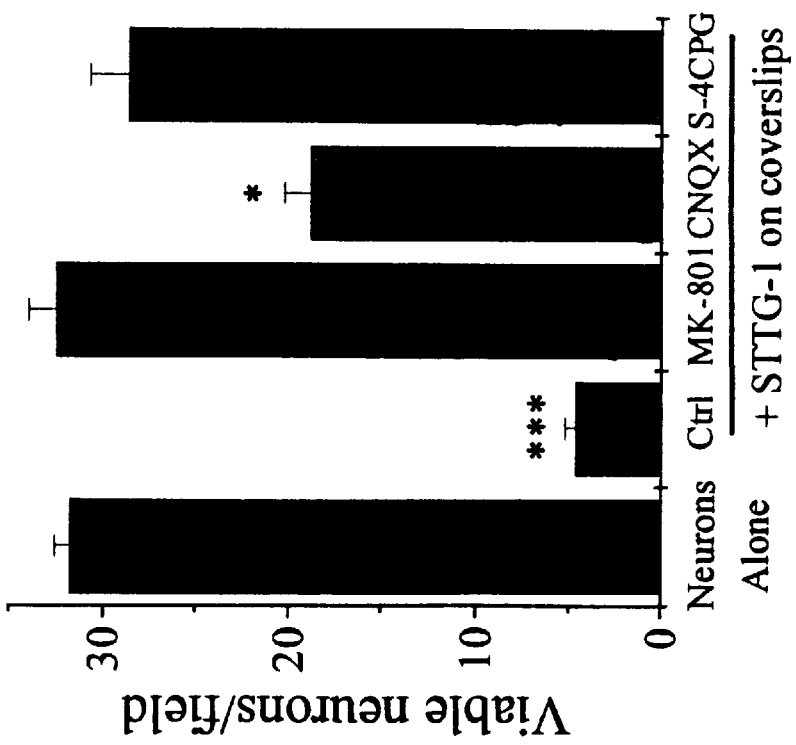
FIG. 7E: Viable neurons were counted 36 h after co-culturing. Neuronal death was almost completely prevented by 10 $\mu$M MK-801 or S-4CPG. CNQX (20 $\mu$M) also reduced the neuronal death from 85% to less than 40%.

In the second set of experiments, glioma cells were cultured on coverslips and placed up-side down in the culture well containing hippocampal neurons. The coverslip and the well were seperated by 1 mm wax spacers to prevent cell-cell contacts such that glioma cells and neurons merely shared a common extracellular space (FIG. 7). These experiments showed similar neurotoxicity by glioma co-culture with >60% loss of neurons. Under these conditions, two major differences were observed from the above co-culture experiments or experiments using glioma-conditioned media: a) albeit less effective than MK-801, which afforded complete protection, 20 $\mu$M CNQX in these co-cultures was neuroprotective, reducing excitotoxicity by >50% (FIG. 7E). This suggests that at rather low glutamate concentrations in co-culture conditions (around 10 $\mu$M) as compared to GCM (100 $\mu$M or higher), constant activation of AMPA/KA receptor may significantly contribute to glutamate induced neuronal damage; and b) significant reduction in neurotoxicity was observed in the outside margins (edge) of the neuronal culture, specifically in areas where glioma cells were at a greater distance (panel F). This suggests that a concentration gradient existed for glutamate released from glioma cells. Furthermore, since S-4CPG inhibits glioma glutamate release, S-4CPG was also very effective in neurotoxicity protection (panel D and E).

DISCUSSION

It was demonstrated herein that glioma cells release sufficient amounts of glutamate to induce wide-spread toxicity in cultured neurons. These data were obtained in seven established glioma cell lines and also in short term primary cultures of glioma cells prepared from biopsy tissues removed from glioma patients. Even when maintained for only minutes in an extracellular volume that exceeded the cellular volume by $10^3$ fold, glioma cells released glutamate in sufficient enough levels to activate NMDA and AMPA/KA receptors on hippocampal neurons and induce delayed, $Ca^{2+}$-dependent cell death. This modus operandi is much different from normal astrocytes, which are poised to maintain low $[Glu]_o$, thereby protecting neurons from glutamate toxicity.

Glutamate concentrations in the culture medium of glioma cells can increase from ~1 $\mu$M to over 100 $\mu$M within 5 h. The toxicity of this medium or glioma cells to neurons could be completely prevented by the NMDA specific inhibitors MK-801 or D-AP5. Significantly, toxicity was still prominent in glioma-neuronal co-culture experiments where cells were grown without contact, but sharing the same extracellular environment. This indicates that even the chronic release of glutamate by glioma cells into a relatively large extracellular space is sufficient to induce neuronal glutamate toxicity. Glutamate released by glioma cells appears to be primarily from metabolized glutamine, although several pathways exist for the de novo synthesis of glutamate from other precursors. Alterations in the speed of glutamate release following changes in the concentrations of several amino acids in the media was observed. Since the tumor tissues are well vascularized and the blood-brain barrier in tumor tissues is hyper-permeable, glioma cells have access to glutamine and other nutrition factors for synthesizing glutamate. There is evidence to suggest an increased ratio of glutamine/glutamate in glioma tissues (44,45). The decrease of total glutamate amount in tumor tissues (44) is likely due to the loss of neurons in these tissues, as neurons contain high levels of glutamate (~10–100 mM). In addition, although changes in $[Glu]_o$ in vivo may determine the neuronal fate, they would not significantly influence the total amount of glutamate in the whole tissue, since the extracellular space only accounts for ~15% of the total tissue volume (46) and $[Glu]_o$ is generally lower than $[Glu]_i$ without exogenous supply.

The studies employing glioma-neuronal co-cultures were aimed at closely mimicking in vivo conditions. In these co-cultures, a balance exists between glutamate release from glioma cells and glutamate uptake into glioma cells and neurons. Since neurons possess a much higher uptake capability than glioma cells, the neuronal uptake of glutamate may play an important role in limiting the $[Glu]_o$ elevation in the co-cultures. This may also explain why the excitotoxicity by glioma cells in the co-culture was not as complete as by glioma-conditioned media, where $[Glu]_o$ had been allowed to build up freely by the release from glioma cells. Since the total glutamate uptake capability is proportional to the number of cells, neurons cultured at higher density were more resistant to glioma cells. Interestingly it was also found that if there was a >20% "contamination" of normal astrocytes in the neuron/glioma co-cultures, neurotoxicity was much less pronounced than in co-cultures essentially free of astrocytes. This is consistent with the neuroprotective role of astrocytes (10) and their ability to remove glutamate very effectively (28). Based on the above reasoning, the combined astrocytic and neuronal glutamate uptake would be expected to greatly retard the process of glioma-induced excitotoxicity as determined in vitro. On the other hand, since the in vitro co-cultures utilized an extracellular space ~$10^4$ fold larger than in vivo, the true speed and extent of [Glu]$_o$ accumulation in vivo may be greatly underestimated. It's conceivable that glutamate released from glioma cells can fill up the narrow in vivo extracellular space much faster than it does in vitro, especially for the extracellular space inside glioma tissue or in the immediate vicinity of the tumor. Slight elevations of [Glu]$_o$ may thus be sufficient to over-activate neuronal glutamate receptors in peritumoral tissue and induce neuronal death or contribute to the seizure activity which is often observed in patients with gliomas (27).

The cause of the impaired glutamate transport by glioma cells remains to be determined. It was recently found that glioma cells express GLAST transporters in levels comparable to normal astrocytes. However, the majority of the immunohistochemically identified transporters are localized to the cell nucleus with very little labeling of the plasma membrane. It is thus conceivable that these transporters are not properly targeted to the plasma membrane, which may account for the observed deficiencies in glutamate transport.

The effect of phenylglycine derivatives to selectively inhibit glutamate release by glioma cells offers exciting clinical potentials for this class of drugs. Reductions in glutamate release from gliomas may reduce neurotoxicity and may slow tumor growth. Moreover, if glutamate release from tumors into the peritumoral brain tissue contributes to seizures, phenylglycine compounds may reduce the likelihood that seizures are triggered from peritumoral neurons. This possibility is particularly exciting in light of the fact that some of the phenylglycine derivatives that were potent inhibitors of glioma glutamate release do not activate synaptic mGluR receptors, and thus, should excerpt very specific effects on the glutamate transport. The mechanism by which these compounds inhibit glutamate release from glioma cells is presently unclear. In a recent study, the effects of these compounds on glial glutamate transport were investigated but were unable to unequivocally delineate the pathway by which they interact with the transporter (38). However, their structural similarity to glutamate suggest that phenylglycine derivatives may bind directly to the glutamate transporter or cell surface proteins that mediate glutamate leaving the cells.

The following references were cited herein:

1. Choi, D. W. Neuron, 1: 623–634,1988.
2. Nicholls, et al. Trends Pharmacol. Sci., 11: 462–468,1990.
3. Storck, T., et al. Proc. Natl. Acad. Sci. U.S.A., 89: 10955–10959,1992.
4. Pines, G., et al. Nature, 360: 464–467,1992.
5. Kanai, Y., and Hediger, M. A. Nature, 360: 467–471,1992.
6. Fairman, W. A., et al. Nature, 375: 599–603,1995.
7. Arriza, et al. Proc. Natl. Acad. Sci. U.S.A., 94: 4155–4160,1997.
8. Torp, R., et al. Europ. J. Neurosci., 6: 936–942,1994.
9. Lehre, K. P., et al. J. Neurosci., 15: 1835–1853,1995.
10. Rothstein, J. D., et al. Neuron, 16: 675–686,1996.
11. Sonnewald, U., et al. Glia, 21: 56–63,1997.
12. Schousboe, et al. Transport of neuroactive amino acids in astrocytes. In: Kettenmann et al. (eds.), Neuroglia, pp. 246–258. New York: Oxford University Press, 1995
13. Kanner, B. I. FEBS Letters, 325: 95–99,1993.
14. Levi, G., and Patrizio, M. J. Neurochem., 58: 1943–1952,1992.
15. Ottersen, O. P. Anat. Embryol., 180: 1–15,1989.
16. Hertz, L., et al. Metabolism of glutamate and related amino acids. In: Norenberg, et al. (eds.), The biochemical pathology of astrocytes, pp. 395–406. New York: Alan R. Liss. 1988.
17. Benveniste, H., et al. J. Neurochem., 43: 1369–1374, 1984.
18. Attwell, D., et al. Neuron, 11: 401–407,1993.
19. Zerangue, N., and Kavanaugh, M. P. Nature, 383: 634–637,1996.
20. Szatkowski, M., et al. Nature, 348: 443–446,1990.
21. Ogata, T., et al. Neurochem. Res., 20: 737–743,1995.
22. Longuemare, et al. J. Neurosci. Res., 40: 379–386,1995.
23. Lipton, et al.. N. Engl. J. Med., 330: 613–622,1994.
24. Paulus, W., and Tonn, J. C. J. Neurooncol., 24: 87–91, 1995.
25. Giese, A., et al. Anticancer Res., 18: 2435–2447,1998.
26. Goldman, C. K., et al. Mol. Biol. Cell., 4: 121–133,1993.
27. Paillas, J. E. J. Neuroradiol., 79–106,1994.
28. Ye, Z. C., and Sontheimer, H. Glia, 22: 237–248,1998.
29. Ye, Z. C., and Sontheimer, H. Neuroreport, 7: 2181–2185,1996.
30. Bradford, M. M. Anal. Biochem., 72: 248–254,1976.
31. Fosse, V. M., et al. J. Neurochem., 47: 340–349,1986.
32. Grynkiewicz, G., et al. J. Biol. Chem., 260: 3440–3450, 1985.
33. Manning, T. J., Jr., and Sontheimer, H. Glia, 20: 163–172,1997.
34. Ince, C., et al. J. Physiol. (London)., 60: 269–275,1983.
35. Whittemore, S. R., et al. Glia, 10: 211–226,1994.
36. Bronfman, M., et al. Anal. Biochem., 255: 252–256, 1998.
37. Velasco, I., et al. J. Neurosci. Res., 44: 551–561,1996.
38. Ye, Z. C., and Sontheimer, H. Glia, 25: 270–281,1999.
39. Hartley, D. M., et al. J. Neurosci., 13: 1993–2000,1993.
40. Brorson, J. R., et al.. J. Neurosci., 14: 187–197,1994.
41. Arias, R. L., et al. Brain. Res., 816: 299–308,1999.
42. Tanaka, T., et al. Jpn. J. Pharmacol., 70: 89–93,1996.
43. Koizumi, S., and Inoue, K. Br. J. Pharmacol., 122: 51–58,1997.
44. Bateman, D. E., et al. Neurol. Res., 10: 112–114,1988.
45. Peeling, et al.. Magn. Reson. Med., 24: 123–136,1992.
46. McBain, C. J., et al. Science, 249: 674–677,1990.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of decreasing neuronal death caused by a primary brain tumor, metastatic brain tumor, or mass brain lesion in an individual in need thereof, comprising the step of:

administering to said individual a pharmacologically effective dose comprising a phenylglycine derivative, wherein said phenylglycine derivative results in a decrease in the amount of glutamate released from a cell, thereby decreasing neuronal death in said individual.

2. The method of claim 1, wherein said phenylglycine derivative is selected from the group consisting of (S)-4-Carboxyphenylglycine (S)-4CPG), (RS)-3,5-Dihydroxyphenylglycine (DHPG), (S)-3-carboxy-4-hydroxyphenylglycine (S-3C4H-PG), (S)-4-carboxy-3-hydroxyphenylglycine (S-4C3H-PG), (R)-4-Carboxyphenylglycine (R-4CPG), (RS)-α-Ethyl-4-carboxyphenylglycine (E4CPG), (RS)-2-Chloro-5-hydroxyphenylglycine (CHPG), (RS)-2-Cyclopropyl-4-phosphonophenylglycine (CPPG), (S)-α-methyl-4-carboxyphenylglycine (MCPG), and (RS)-α-methyl-4-tetrazolylphenylglycine (MTPG).

3. The method of claim 1, wherein said phenylglycine derivative is administered to said individual in an amount of from about 0.4 mg/kg to about 40 mg/kg.

4. A method of treating a primary brain tumor, metastatic brain tumor, or mass brain lesion associated with glutamate released from glioma cells, comprising the step of:
contacting said cells with an effective amount of a pharmaceutical composition comprising a phenylglycine derivative, wherein said phenylglycine derivative results in an inhibition in the amount of glutamate released from glioma cells.

5. The method of claim 4, wherein said phenylglycine derivative is selected from the group consisting of (S)-4-Carboxyphenylglycine (S-4CPG), (RS)-3,5-Dihydroxyphenylglycine (DHPG), (S)-3-carboxy-4-hydroxyphenylglycine (S-3C4H-PG), (S)-4-carboxy-3-hydroxyphenylglycine (S-4C3H-PG), (R)-4-Carboxyphenylglycine (R-4CPG), (RS)-α-Ethyl-4-carboxyphenylglycine (E4CPG), (RS)-2-Chloro-5-hydroxyphenylglycine (CHPG), (RS)-2-Cyclopropyl-4-phosphonophenylglycine (CPPG), (S)-α-methyl-4-carboxyphenylglycine (MCPG), and (RS)-α-methyl-4-tetrazolylphenylglycine (MTPG).

6. The method of claim 5, wherein said phenylglycine derivative is administered to said individual in an amount of from about 0.4 mg/kg to about 40 mg/kg.

7. The method according to claim 4, wherein a symptom associated with said brain tumor or brain lesion is epileptic seizures.

* * * * *

UNITED STATES PATENT AND TRADEMARK OFFICE
CERTIFICATE OF CORRECTION

PATENT NO.     : 6,197,820 B1
DATED          : March 6, 2001
INVENTOR(S)    : Harald J. Sontheimer et al.

It is certified that error appears in the above-identified patent and that said Letters Patent is hereby corrected as shown below:

<u>Title page,</u>
Item [60], Related U.S. Application Data, delete "Provisional application No. 60/080,859, filed on April 6, 1998".

Signed and Sealed this

Twenty-second Day of November, 2005

JON W. DUDAS
*Director of the United States Patent and Trademark Office*